US009857371B2

(12) United States Patent
Brujic et al.

(10) Patent No.: US 9,857,371 B2
(45) Date of Patent: Jan. 2, 2018

(54) BIOMIMETIC EMULSIONS

(71) Applicant: New York University, New York, NY (US)

(72) Inventors: Jasna Brujic, New York, NY (US); Lea-Laetitia Pontani, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 226 days.

(21) Appl. No.: 13/889,083

(22) Filed: May 7, 2013

(65) Prior Publication Data

US 2013/0302406 A1    Nov. 14, 2013

Related U.S. Application Data

(60) Provisional application No. 61/644,290, filed on May 8, 2012.

(51) Int. Cl.
| | | |
|---|---|---|
| *G01N 33/569* | (2006.01) |
| *A61K 9/107* | (2006.01) |
| *A61K 47/24* | (2006.01) |
| *A61K 47/54* | (2017.01) |
| *A61K 47/62* | (2017.01) |
| *A61K 47/69* | (2017.01) |

(52) U.S. Cl.
CPC ....... *G01N 33/56966* (2013.01); *A61K 9/107* (2013.01); *A61K 47/24* (2013.01); *A61K 47/557* (2017.08); *A61K 47/62* (2017.08); *A61K 47/6907* (2017.08); *A61K 47/6911* (2017.08)

(58) Field of Classification Search
None
See application file for complete search history.

(56) References Cited

U.S. PATENT DOCUMENTS

| | | | | |
|---|---|---|---|---|
| 5,653,996 | A | * | 8/1997 | Hsu ............................. 424/450 |
| 6,645,528 | B1 | * | 11/2003 | Straub ................. A61K 9/1611 424/489 |
| 7,785,617 | B2 | * | 8/2010 | Shakesheff .......... A61K 9/0024 424/426 |
| 2006/0078624 | A1 | * | 4/2006 | Zalipsky ............. A61K 9/1617 424/489 |
| 2007/0092558 | A1 | * | 4/2007 | Heavner et al. ............. 424/450 |
| 2009/0098272 | A1 | | 4/2009 | Banken |
| 2009/0162425 | A1 | * | 6/2009 | Divi et al. ................... 424/450 |
| 2009/0275465 | A1 | | 11/2009 | Gang et al. |

OTHER PUBLICATIONS

Pontani L-L, Biomimetic emulsions reveal the effect of mechanical forces on cell-cell adhesion, PNAS, 2012, 109, 25, 9839-9844.*
Adams, Cynthia L., et al., "Mechanisms of Epithelial Cell-Cell Adhesion and Cell Compaction Revealed by High-resolution Tracking of E-Cadherin-Green Flourescent Protein", The Journal of Cell Biology, vol. 142, No. 4, Aug. 24, 1998, pp. 1105-1119.

(Continued)

*Primary Examiner* — Celeste A Roney
(74) *Attorney, Agent, or Firm* — Foley & Lardner LLP

(57) ABSTRACT

A biomimetic system is provided for use in modeling cell-cell adhesion mechanisms comprising functionalized emulsion droplets. Further, a cell culture medium and a drug delivery system using said biomimetic system are provided.

13 Claims, 5 Drawing Sheets

(56) References Cited

OTHER PUBLICATIONS

Angres, Brigitte, et al., "Mechanism for Transition from Initial to Stable Cell-Cell Adhesion: Kinetic Analysis of E-Cadherin-Mediated Adhesion Using a Quantitative Adhesion Assay", The Journal of Cell Biology, vol. 134, No. 2, Jul. 1996, pp. 549-557.
Atilgan, Erdinc et al., "Nucleation and Growth of Integrin Adhesions", Biophysical Journal, vol. 96, May 2009, pp. 3555-3572.
Bourouina, Nadia, et al., "Formation of Specific receptor-ligand bonds between liquid interfaces", The Royal Society of Chemistry 2001, Soft Matter, 2011, 7, pp. 9130-9139.
Brujic, Jasna, "Measuring the Coordination No. Of Entropy of a 3D Jammed Emulsion Packing by Confocal Microscopy", Physical Review Letters, Jun. 15, 2007, pp. 248001-248004.
Brujic, Jasna et al., "3D bulk measurements of the force distribution in a compressed emulsion system", The Royal Society of Chemistry 2003, pp. 207-220.
Chen, Chien Peter et al., "Specificity of cell-cell adhesion by classical cadherins: Critical role for low-affinity dimerization through β-strand swapping", www.pnas.org/cgi/doi/10.1073/onas. 0503319102, PNAS, Jun. 14, 2004, vol. 102, No. 24, pp. 8531-8536.
Cuvelier, Damien et al., "Hidden Dynamics of Vesicle Adhesion Induced by Specific Stickers", Physical Review Letters, Nov. 26, 2004, pp. 228101-1 to 228101-4.
Douezan, Stephane, et al., "Spreading dynamics and wetting transition of cellular aggregates", PNAS, May 3, 2011, vol. 108, No. 18, pp. 7315-7320.
Du Roure, O., et al., "Homophilic Interactions between Cadherin Fragments at the Single Molecule Level: An AFM Study", Langmuir, vol. 11, No. 10, 2006, pp. 4680 to 4684.
Fattaccioli, Jacques et al., "Specific wetting probed with biomimetic emulsion droplets", www.rsc.org/softmatter, Soft Matter, 2008, vol. 4., pp. 2434,2440.
Foty, Ramsey A., "Surface tensions of embryonic tissues predict their mutual development behavior", The Company of Biologists Limited 1996, Development 122, pp. 1611-1620 (1996).
Helmlinger, Gabriel, "Solid stress inhibits the growth of multicellular tumor spheroids", Nature Biotechnology, vol. 15, Aug. 1997, pp. 778-783.
Panorchan, Porntula, "Single-molecule analysis of cadherin-mediated cell-cell adhesion", Journal of Cell Science 119, Sep. 28, 2005, pp. 66-74.
Pautot, Sophie et al., "Engineering Asymmetric Vesicles", PNAS, Sep. 16, 2003, vol. 100, No. 19, pp. 10718-10721.
Tambe T. Dhananjay et al., "Collective cell guidance by cooperative intercellular forces", Nature Materials, vol. 10, Jun. 2011, pp. 469-475.
Vasioukhin, Valeri et al., "Directed Actin Polymerization Is the Driving Force for Epithelial Cell-Cell Adhesion", Cell, vol. 100, Jan. 21, 2000, pp. 209-219.
Yuan, Chunbo et al., "Energy Landscape of Streptavidin—Biotin Complexes Measured by Atomic Force Microscopy", Biochemistry 2000, vol. 39, pp. 10219-10223.
Basan, Markus, et al., "Dissipative particle dynamics simulations for biological tissues: reheology and competition", Phys. Biol. 8 (2001) pp. 1-13.
Bell, George I., "Models for the Specific Adhesion of Cells to Cells", Science vol. 200, May 12, 1978, pp. 618-627.
Borghi, Nicolas, et al., "Regulation of cell motile behavior by crosstalk between cadherin- and integrin-mediated adhesions", PNAS, Jul. 27, 2010, vol. 107, No. 30, pp. 13324-13329.
Bruinsma, Robijn et al., "Adhesive switching of membranes: Experiment and theory", Physical Review E. vol. 61, No. 4., Apr. 2000, pp. 4253-4267.
Chu, Yeh-Shiu, et al., "Force Measurements in E-cadherin-mediated cell doublets reveal rapid adhesion strengthened by actin cytoskeleton remodeling through Rac and Cdc42", The Journal of Cell Biology, Vo. 167, No. 6, Dec. 20, 2004, pp. 1183-1194.
Foty, Ramsey A., "The differential adhesion hypothesis: a direct evaluation", Development Biology, 278 (2005), pp. 255-263.
Guevorkian, Karien et al., "Aspiration of Biological Viscoelastic Drops", Physical Review Letters, vol. 104, May 28, 2010, pp. 218101-1 to 218101-4.
Ladoux, Benoit et al., "Strength Dependence of Cadherin-Mediated Adhesions", Biophysical Journal, vol. 98, Feb. 2010, pp. 534-542.
Liu, Zhijun, et al., "Mechanical tugging force regulates the size of cell-cell junctions", PNAS, Jun. 1, 2010, vol. 107, No. 22, pp. 9944-9949.
Mahaffy, R.E., "Scanning Probe-Based Frequency-Dependent Microrheology of Polymer Gels and Biological Cells", Physical Review Letters, Jul. 24, 2000, vol. 85, No. 4, pp. 880-883.
Manning, Lisa N., "Coaction of intercellular adhesion and cortical tension specifies tissue surface tension", PNAS, Jul. 13, 2010, vol. 107, No. 28, pp. 12517-12522.
Papusheva, Ekaterina, et al., "Spatial Organization of adhesion: force-dependent regulation and function in tissue morphogenesis", The EMBO Journal, vol. 29, No. 16, 2010, pp. 2753-2768.
Perez-Moreno, Mirna et al., "Sticky Business: Orchestrating Cellular Signals at Adherens Junctions", Cell, vol. 112, Feb. 21, 2003, pp. 535-548.
Sackmann, Erich, et al., "Cell Adhesion as Wetting Transition?", ChemPhysChem, 2002, vol. 3, pp. 262-269.
Thiery, Jean Paul et al., "Complex networks orchestrate epithelial-mensenchymal transitions", Molecular Cell Biology, vol. 7, Feb. 2006, pp. 131-142.
Thiery, Jean Paul, "Cell adhesion in development: a complex signaling network", Current Opinion in Genetics & Development 2003, vol. 13, pp. 365-371.
Yap, Alpha S., et al., "Direct cadherin-activated cell signaling: a view from the plasma membrane", The Journal of Cell Biology, vol. 160, No. 1, Jan. 6, 2003, pp. 11-16.
Walker, Scott A., et al., "Controlled Multi-Stage Self-Assembly of Vesicles", Matt. Res. Soc, Symp. Proce., vol. 372, 1995, pp. 95-100.
Hadorn et al., Specific and reversible DNA-directed self-assembly of oil-in-water emulsion droplets, PNAS, Dec. 11, 2012, vol. 109, No. 50, pp. 20320-20325.
Pontani, et al., Biomimetic emulations reveal the effect of mechanical forces on cell-cell adhesion, PNAS, Jun. 19, 2012, vol. 109, No. 25, pp. 9839-9844.
U.S. Office Action for U.S. Appl. No. 14/266,026, dated Feb. 23, 2016, 12 pages.
U.S. Office Action for U.S. Appl. No. 14/266,026, dated Sep. 11, 2015, 18 pages.
U.S. Office Action for U.S. Appl. No. 14/266,026, dated Aug. 25, 2016, 10 pages.

* cited by examiner

Figure 2A
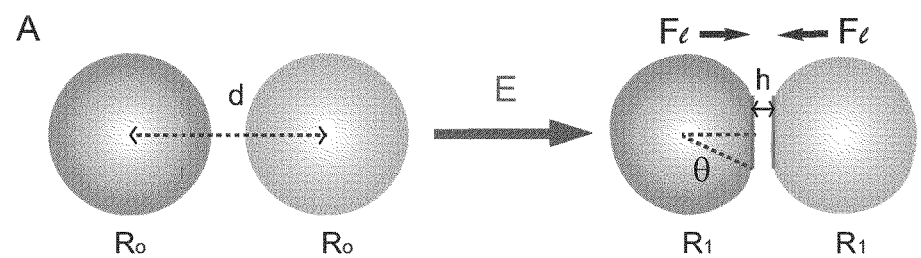
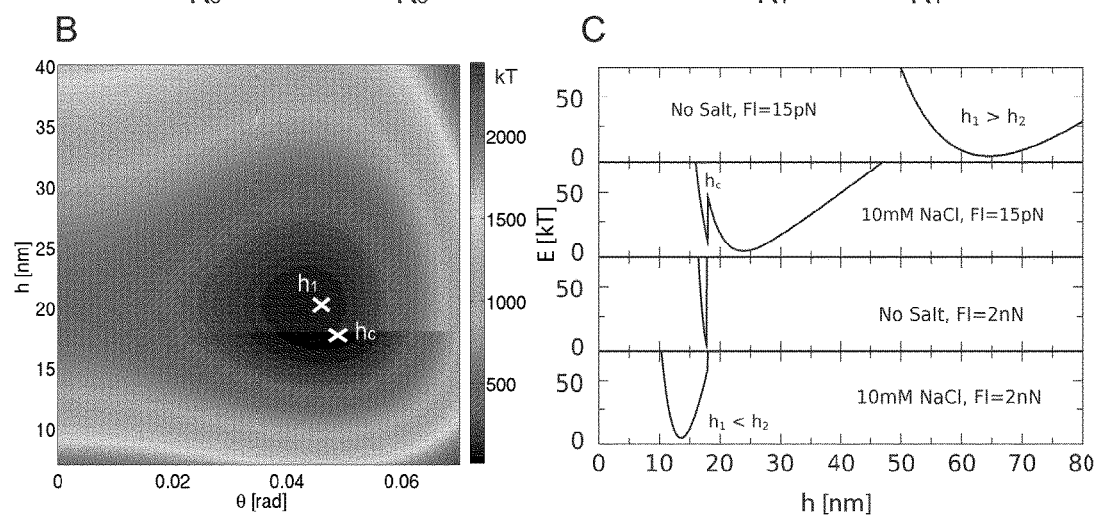
Figure 2B
Figure 2C

Figure 3A
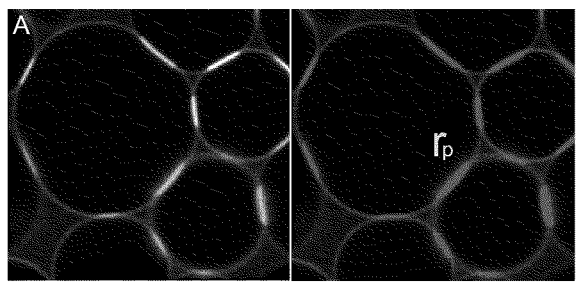
Figure 3C
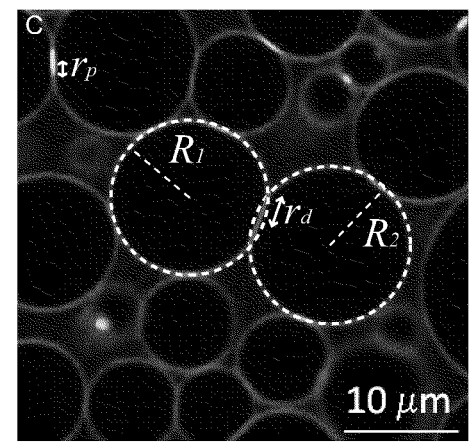
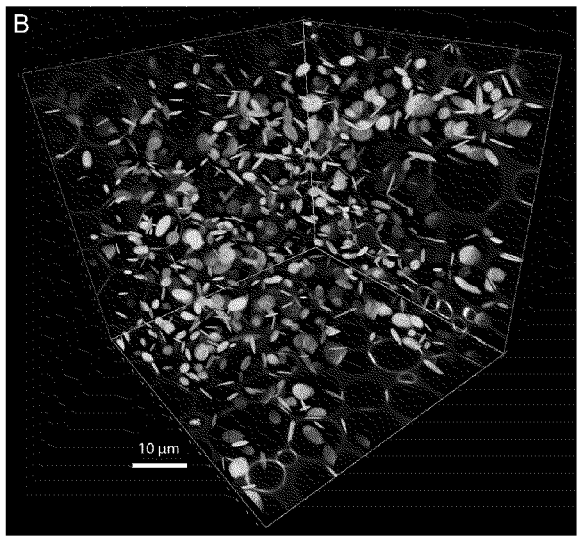
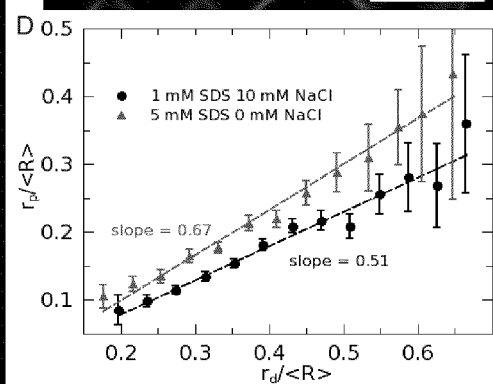
Figure 3B
Figure 3D

Figure 4A
Figure 4B
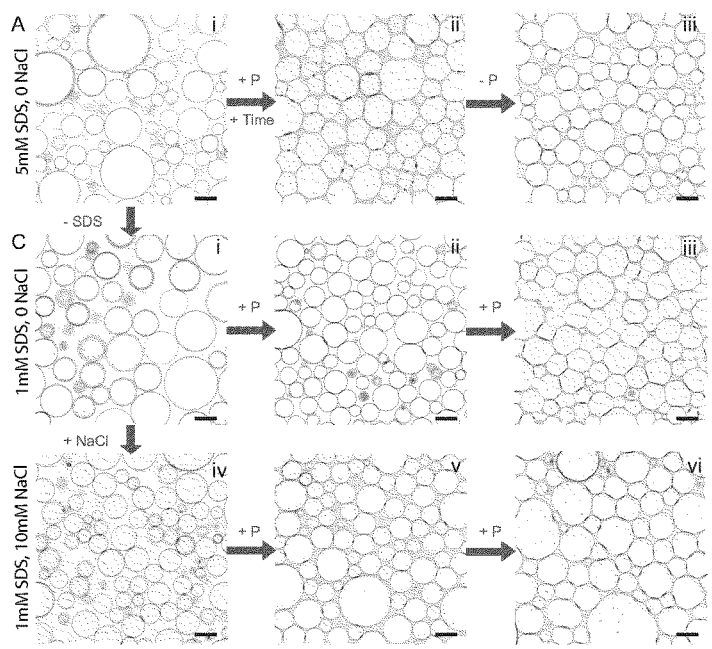
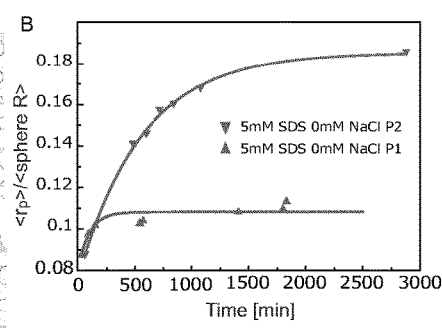
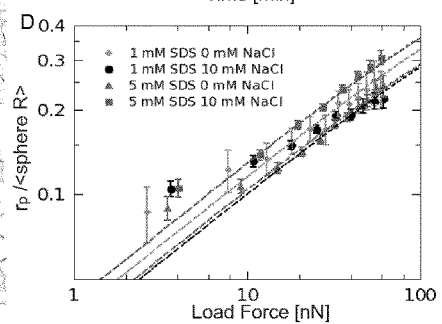
Figure 4C
Figure 4D

Figure 5A
Figure 5C
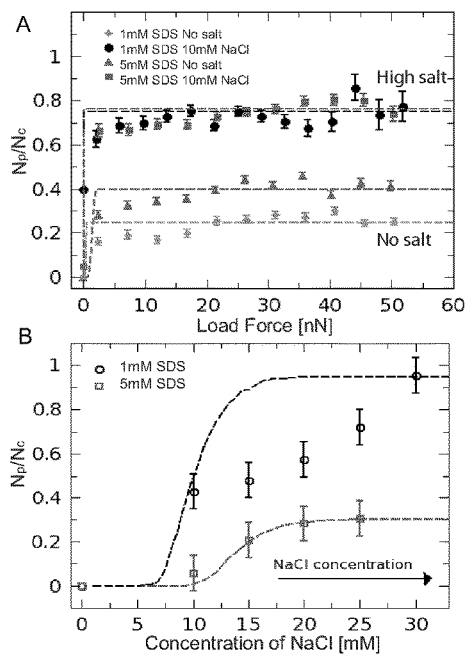
Figure 5B
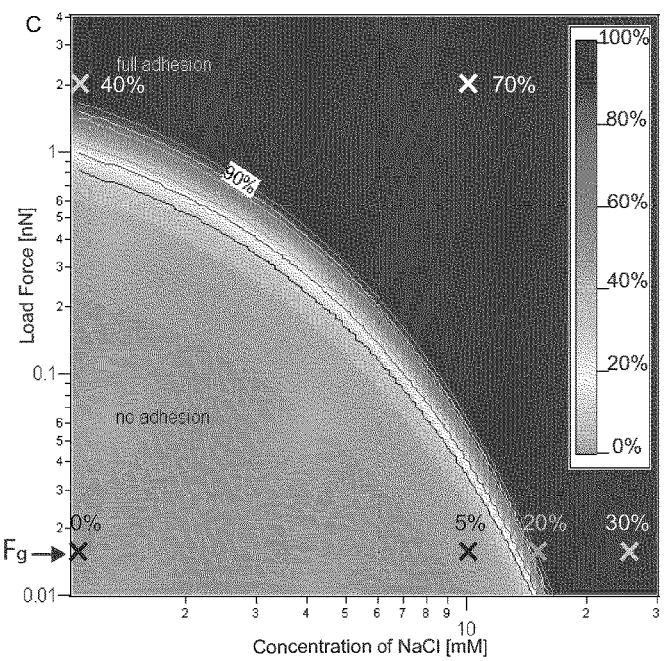

BIOMIMETIC EMULSIONS

CROSS-REFERENCE TO RELATED APPLICATIONS

This application claims priority from U.S. Provisional Patent Application 61/644,290 filed May 8, 2012 which is hereby incorporated by reference in its entirety.

STATEMENT OF GOVERNMENT-SPONSORED RESEARCH

This invention was made with United States government support awarded by the following agencies: United States National Science Foundation, Career Award 0955621. The United States government has certain rights in the invention.

FIELD OF THE INVENTION

The present invention relates generally to cell-cell adhesion mechanisms to enable control of selected chemical and biological processes for commercial applications. More particularly, the present invention relates to biomimetic systems for modeling and methods of increasing likelihood of cell-cell adhesion and exploitation of this information for commercial purposes.

BACKGROUND OF THE INVENTION

Cell-cell adhesion is a fundamental biological function. It underlies the structure of tissues and their dynamic reorganization during processes as important as morphogenesis, cell locomotion and signaling. In addition to the high level of complexity in the identified biochemical pathways, it has recently become clear that mechanical effects also play an important role. For example, pushing cells together or increasing their contractile forces by changing the substrate stiffness reinforces the strength of contacts. Furthermore, since homeostatic pressure arising from the balance of cell division and cell death is important in achieving the mechanical integrity of tissues it is also assumed to affect cell-cell adhesion. However, the physical origin of force-sensitive adhesion remains an open question. This is so particularly because the theoretical models used for relevant study are derived from the behavior of simplified model membranes that lack mechanical resilience.

Although these models successfully describe the kinetics and energetics of adhesion in the absence of rigidity, they cannot address the effects of force. In a cell, rigidity arises from the cytoskeleton scaffold and mechanical coupling with neighboring cells in the surrounding tissue. As a result, individual cells are viscoelastic with a bulk modulus of about 1 kPa. Moreover, the interplay between cortical tension and adhesive interactions with neighbors gives rise to a surface tension in cellular aggregates.

Biomimetic modeling that describes all aspects of cellular interaction, including the effects of force, is essential for exploring avenues of treatment of diseases characterized by abnormal cell-cell adhesion. Otherwise, entire avenues of treatment might lie unexplored. Such diseases span a vast swath of pathology, but may be exemplified by the following: human genetic diseases may be caused by inability to express a specific adhesion molecule, such as in leukocyte adhesion deficiency-I (LAD-I), where patients do not express the β2-integrin subunit precursor. This integrin is required for leukocytes to adhere to the blood vessel wall during inflammation in order to fight infection. The leukocytes from LAD-I patients fail to adhere and patients exhibit serious episodes of infection that can be life threatening. Additionally, in tumor metastasis, tumors that spread through the circulatory system use mechanisms of cell adhesion to establish new tumors in the body. Still further, many viruses also have adhesion molecules required for viral binding to host cells. For example, influenza virus has a hemagglutinin on its surface that is required for recognition of the sugar sialic acid on host cell surface molecules. HIV has an adhesion molecule termed gp120 that binds to its ligand CD4, which is expressed on lymphocytes.

Therefore, there remains a need for novel approaches to treatment of these conditions, which can be provided by the development of a biomimetic system capable of replicating the effects of force on cell-cell adhesion in order to form a proper understanding of the effects of such force on cellular interactions. Such understanding will allow applications to chemical and biological systems for commercial uses.

SUMMARY OF THE INVENTION

The present invention relates to novel assays and therapeutic methods developed using a model created to address the problems with existing systems outlined above.

In particular, the present invention provides a biomimetic emulsion system for use in determining the force necessary to promote cell-cell adhesion in a human sample in which elasticity is introduced through an interfacial tension of about 10 mN/m to match that found in cell aggregates and embryonic tissues. Furthermore, the present invention mimics the dense packing of cells in tissue by compressing the 3-dimensional assembly of droplets at about 10 kPa, to match the measured homeostatic pressure in tissues. In addition to mechanical similarities, the chemical composition of the present system reproduces the attractive and repulsive interactions that govern between cells. The system is used to demonstrate the conditions under which a pushing force is necessary to create adhesion, showing that actin-mediated forces are a prerequisite for cell-cell adhesion.

In one aspect, a biomimetic system is provided, comprising at least two functionalized emulsion droplets, each having at least one surface active agent selected from the group consisting of: an interfacial phospholipid component, a surfactant causing electrostatic repulsion, a polymer to induce steric repulsion, and a ligand that facilitates adhesion; and wherein the aqueous phase of the emulsion comprises an agent with a functional group that binds to the ligand, and wherein the phospholipid component facilitates the formation of emulsion droplets that are each at least 1 micron in diameter. In some embodiments, the ligand may be biotin. In further embodiments, the agent may be streptavidin, the interfacial phospholipid component may be an egg phosphatidylcholine, or the surfactant may be sodium dedcyl sulfate ionic surfactant. In yet further embodiments, the polymer may be selected from the group consisting of polyethylene glycol (PEG), polypropylene glycol (PPG), carbohydrate polymer, amino acid polymer or polyvinyl pyrolidone. In yet further embodiments, the polymer and the ligand may form a single surface active complex. Additionally, the agent may, once bound to the ligand of one droplet surface, diffuse until it binds to another agent on a neighboring surface. In further embodiments, force may be applied to the system in an amount sufficient to reduce the interparticle distance, h, to be smaller than a critical length $h_c$, below which the interaction of the surface active agents produces an adhesive state. In such an embodiment, the ligand may be biotin, the agent may be streptavidin, and the $h_c$ may be about 18 nm. The force may, in further embodiments, be applied either via centrifuge or the addition of a salt.

Another aspect of the present invention provides a drug delivery system comprising at least one functionalized emulsion droplet containing an active ingredient suspended in the oil phase, each droplet comprising: an interfacial phospholipid component, and a ligand that facilitates adhesion; and wherein a target cell has at least one surface active agent with a functional group that binds to the ligand, and wherein the at least one emulsion droplet is greater than 1 micron in diameter, such as, in some embodiments, between 5 and 20 microns in diameter. In some embodiments, the interfacial phospholipid component may be an egg phosphatidylcholine. In further embodiments, the at least one emulsion droplet further comprises a polymer selected from the group consisting of polyethylene glycol (PEG), polypropylene glycol (PPG), carbohydrate polymer, amino acid polymer or polyvinyl pyrolidone. In still further embodiments, the system may further comprise a fluorescent dye to add color to the emulsion. The emulsion droplets, in some embodiments, are formulated for topical or transdermal administration. The formulation may include liposzone, liposomes, dual emulsion liposomes, micelles, or microspheres, and, in further embodiments, may take the form of a cream, a lotion, a gel, an ointment, a paste, or a solution.

Yet another aspect of the present invention provides a method of increasing the density or viscosity of a formulation comprising at least one emulsion droplet, comprising the step of increasing the concentration of surface active agents embedded in the interfacial phospholipid component. Still another aspect of the present invention provides a method of decreasing the density or viscosity of the formulation comprising at least one emulsion droplet, comprising the step of decreasing the concentration of surface active agents embedded in the interfacial phospholipid component.

Still another aspect of the present invention provides a cell culture medium with tunable elastic properties comprising at least two functionalized emulsion droplets, each having at least one surface active agent selected from the group consisting of: an interfacial phospholipid component, a surfactant causing electrostatic repulsion, a polymer to induce steric repulsion, and a ligand that facilitates adhesion; and wherein the aqueous phase of the emulsion comprises an agent with a functional group that binds to the ligand; wherein the at least two emulsion droplets are each greater than 1 micron in diameter; and wherein the elasticity of the medium increases when the concentration of surface active agents decreases, and the elasticity of the medium decreases when the concentration of surface active agents increases. In some embodiments, the ligand is biotin. In further embodiments, the agent is streptavidin. The interfacial phospholipid component is, in some embodiments, an egg phosphatidylcholine. In yet further embodiments, the surfactant may be a sodium dodecyl sulfate ionic surfactant. The polymer may be selected from the group consisting of polyethylene glycol (PEG), polypropylene glycol (PPG), carbohydrate polymer, amino acid polymer or polyvinyl pyrolidone. The polymer may further, in some embodiments, form a single surface active complex with the ligand. Additionally, the agent may, once bound to the ligand of one droplet surface, diffuse until it binds to another agent on a neighboring surface. Force may be applied to the system in an amount sufficient to reduce the interparticle distance h to be smaller than a critical length $h_c$, below which the interaction of the surface active agents produces an adhesive state. In some embodiments, the ligand may be biotin, the agent may be streptavidin, and may be about 18 nm. The force may, in some embodiments, be applied either via centrifuge or the addition of a salt. In yet further embodiments, the cell culture medium may further comprise a fluorescent dye to add color to the emulsion.

Yet another aspect of the present invention provides a method of treatment of a disease characterized by inadequate cell-cell adhesion comprising administering to a human in need thereof a pharmacological agent that causes an increase in the homeostatic pressure exerted on the cells. The disease may, in some embodiments, be leukocyte adhesion deficiency-I (LAD-I).

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "active agent" is used herein to refer to a chemical material or compound that induces a desired beneficial effect when administered topically or subcutaneously, and includes agents that are therapeutically and/or prophylactically effective as pharmaceuticals ("pharmacologically active agents"). By an "effective" amount of an active agent is meant a nontoxic but sufficient amount of an active agent to provide the desired beneficial effect.

The term "emulsion," as used herein, includes dispersions or droplets, as well as other lipid structures that can form as a result of hydrophobic forces that drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. The droplets have an average diameter of between about 5-20 microns.

The term "surfactant" refers herein to any molecule having both a polar head group, which energetically prefers solvation by water, and a hydrophobic tail which is not well solvated by water. The term "cationic surfactant" refers to a surfactant with a cationic head group. The term "anionic surfactant" refers to a surfactant with an anionic head group. Other surfactant include non-ionic and zwitterionic surfactants.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 2(A) is a depiction of idealized droplet deformation under a compressive force $F_j$. The total energy E depends on the inter-cellular distance h and the deformation angle θ. 2(B) shows a typical energy landscape as a function of the deformation parameters. Patch adhesion occurs when the global energy minimum is located at h≤hc. 2(C) is a line graph showing the model prediction that two droplets adhere spontaneously either by the addition of salt or applied force.

FIG. 3(A) is a pair of micrographs in which the radii of fluorescent adhesive patches are determined by thresholding the intensity of the image; FIG. 3(B) is a depiction of the adhesive patches as placed in the 3D structure of the packing; FIG. 3C illustrates the radii of deformation between droplets as derived from the overlap between identified spheres of radii R1 and R2; and FIG. 3D is a line graph showing the linear correlation between the adhesion and deformation radii of each contacting droplet pair in the packing.

FIG. 4A illustrates two-dimensional confocal slices of the system under different conditions. When the droplets are stabilized with 5 mM SDS, centrifugation and waiting time are necessary to observe the formation of adhesive patches, which are irreversible. 4(B) is a line graph showing the growth of the mean adhesive radius for the emulsion in 4(A), and is shown for two different applied compressions corresponding to average forces of F1=26 nN, and F2=42 nN, and fit with exponentials. 4(C) is another series of confocal slices demonstrating that lowering the SDS concentration to 1 mM still requires compression to induce adhesion (Ci-iii). However, when salt is added to the solution (4Civ-vi), gravity alone triggers droplet adhesion and the patches formed under compression are more numerous (4Cvi) than in the salt-free cases (4Aiii, 4Ciii). 4(D) is a line graph showing that the normalized patch radius for all emulsion conditions grows as a function of the applied force, in agreement with the model at high forces (dashed lines).

FIG. 5(A) is a line graph showing the increase of the probability of finding a patch as a function of the applied force, or, in FIG. 5(B), the salt concentration. The observed trends are predicted by the model phase diagram of 5(C), in which the experimental fraction of adhesive contacts are labeled as crosses and overlaid with the model phase diagram.

Figure 1A:
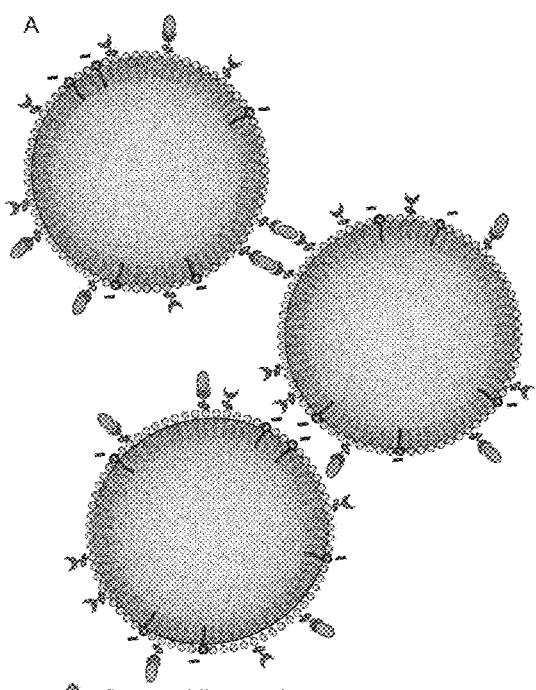
FIG. 1(A) is a schematic representation of functionalized emulsions used in the present systems. The oil/water interface is stabilized by a mixture of phospholipids and negatively charged SDS. Some lipids hold a PEG-biotin group that allows binding through biotin-streptavidin interactions, as shown on the upper droplets.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF THE PREFERRED EMBODIMENTS

The present invention relates to a biomimetic system comprising functionalized emulsion droplets, each having at least one surface active agent selected from the group consisting of: an interfacial phospholipid component, a surfactant causing electrostatic repulsion, a polymer to induce steric repulsion, and a ligand that facilitates adhesion; and wherein the aqueous phase of the emulsion comprises an agent with a functional group that binds to the ligand.

The aqueous phase of the emulsion may be water or a buffer, including a physiologically compatible solution such as water or phosphate buffered saline.

Any suitable polymer may be used. In some embodiments, the polymer may be selected from the group consisting of polyethylene glycol (PEG), polypropylene glycol (PPG)), carbohydrate polymer, amino acid polymer or polyvinyl pyrolidone. In preferred embodiments, the polymer is PEG.

The skilled artisan will understand that a variety of lipid components can be used to formulate the emulsions used in the present invention, such as, for example, cardiolipin, phosphatidylglycerol, Cholesterol (CH), alpha-tocopherol (a-T), egg phosphatidylcholine (EPC), and egg phosphatidylglycerol (EPG).

Any pharmaceutically acceptable surfactant may be utilized in the hormone emulsion compositions of the invention, including ionic, non-ionic, anionic, cationic, and zwitterionic surfactants. Exemplary surfactants that may be used in the emulsion compositions of the invention include, but are not limited to, non-phospholipid surfactants, such as the Tween family of surfactants (polyoxyethylene derivatives of sorbitan fatty acid esters; e.g., Tween 20, Tween 60, and Tween 80), nonphenol polyethylene glycol ethers, sorbitan esters (such as Span and Arlacel), glycerol esters (such as glycerin monostearate), polyethylene glycol esters (such as polyethylene glycol stearate), poloxamers or block polymers (such as Pluronics, e.g., Pluronic F68), acrylic polymers (such as Pemulen), ethoxylated fatty esters (such as Cremophor RH-40), ethoxylated alcohols (such as Brij), ethoxylated fatty acids, monoglycerides, silicon based surfactants, polysorbates, Tergitol NP-40 (Poly(oxy-1,2-ethanediyl), α-(4-nonylphenol)-.omega.-hydroxy, branched [molecular weight average 1980]), and Tergitol NP-70 (a mixed surfactant—AQ=70%).

In some embodiments, the surfactant may be selected from the group consisting of, but not limited to, sorbitan esters, glycerol esters, polyethylene glycol esters, poloxamers, block polymers, acrylic polymers (such as Pemulen), ethoxylated fatty esters (such as Cremophor RH-40), ethoxylated alcohols (such as Brij), ethoxylated fatty acids (such as Tween), monoglycerides, silicon based surfactants, and polysorbates. In a preferred embodiment, the surfactant may be a sodium dedcyl sulfate ionic surfactant.

Preferably, the individual surfactant molecules are free of cross-linkages. The surfactant is also preferably soluble in water. One or more surfactants may be used in the compositions and methods of the invention.

Furthermore, any ligand-agent pair may be used to facilitate adhesion of the model. In preferred embodiments, the ligand is biotin and the agent is streptavidin.

Additional compounds suitable for use in the emulsion compositions of the invention include but are not limited to bulking agents, coloring agents, pharmaceutically acceptable excipients, a preservative, pH adjuster, buffer, etc. The additional compounds can be admixed into a previously emulsified emulsion, or the additional compounds can be added to the original mixture to be emulsified. In certain of these embodiments, one or more additional compounds are admixed into an existing emulsion composition immediately prior to its use.

Suitable preservatives in the emulsion compositions of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocopherol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof.

The emulsion compositions may further comprise at least one pH adjuster. Suitable pH adjusters in the emulsions of the invention include, but are not limited to, diethylanolamine, lactic acid, monoethanolamine, triethylanolamine, sodium hydroxide, sodium phosphate, semi-synthetic derivatives thereof, and combinations thereof.

The invention further provides a drug delivery system comprising an emulsion as described above, which may contain an active agent or ingredient suspended in the oil phase of the emulsion for delivery to a location near a target cell. Such a system may be formulated with other pharmaceutically acceptable excipients, and may be suitable for topical or transdermal administration for cosmetic or therapeutic uses. The formulation may be in any form suitable for application to the skin. For example, it may take the form of a cream, a lotion, a gel, an ointment, a paste, or a solution. The formulation may include lipozone, liposomes, dual emulsion liposomes (water-oil-water), micelles, or microspheres. The formulation may be: a cosmetic composition that includes in addition to the stabilizers and the active ingredients water and other additives that are normally used in cosmetics. For example, it may include thickening agents, preservatives, emulsifiers, perfumes, dyes or coloring, vegetable or mineral oil, antiseptic agents, acidifying or alkalizing agents, vitamins, anti-UV agents, surfactant, solvents, pH stabilizing agents, and other active ingredients known to be effective on the skin. The cosmetic composition may be provided as a milk, cream, lotion, serum, mask or gel. The droplets may further be coated with a polymer such as polyethylene glycol to ensure compatibility with in vivo tissues and avoid an immune response.

The drug delivery system may be administered for therapy by any suitable route including oral, nasal, topical (including transdermal, aerosol, buccal and sublingual), parenteral (including subcutaneous, intramuscular, intravenous and intradermal) and pulmonary. It will also be appreciated that the preferred route will vary with the condition and age of the recipient, the nature of the active agent, and the disease being treated.

The properties of the emulsions described herein may be altered or tuned to suit the needs imposed by the use to which the emulsion will be put. In particular, as described more fully in the working examples provided below, the adhesive properties of the emulsion may be altered by the application of force to the system. Such a force may be applied by any mechanical or chemical means, such as, for example, centrifugation or the addition of a salt solution. Further, the adhesive and elastic properties of the emulsion may be modified by changing the concentration of surface active proteins on each emulsion droplet, with a greater concentration resulting in greater adhesion and less elasticity, and a lower concentration resulting in less adhesion and greater elasticity.

The emulsions described herein may further comprise a coloring agent to tint or dye the emulsion any desired shade. In preferred embodiments, the coloring agent is a fluorescent dye. Useful dyes include, but are not limited to, e.g., Cy5®, Cy3®, FITC, rhodamine, lanthamide phosphors, Texas red, FAM, JOE, Cal Fluor Red 610®, and Quasar 670®. In further embodiments, the emulsions described herein may be tuned to match the refractive indices of the oil and water phases in order to achieve optical transparency.

EXAMPLES

Example 1: Model for Adhesion Between Droplets in System

To quantitatively assess the role of force in cell-cell adhesion, and develop useful understanding of cell-cell adhesion, a local model was developed to take into account the various energy terms that play a role in the interaction between two cells in contact, as illustrated by the schematic in FIG. 2(A). The binding energy $E_b$ of the lock and key proteins and the work $W_1$ done by the external pressure both favor adhesion. By contrast, the electrostatic repulsion $E_e$ and the surface energy $E_d$ oppose adhesive patch formation. Van der Waals interactions, which are negligible in cell-cell contacts, are ignored as the system is refractive index matched. For a given set of experimental conditions, the minimization of the total free energy according to Equation (I)

$$E = E_d + E_e + E_b + W_1 \qquad (I)$$

With respect to the distance h between the droplet surfaces and the deformation angle θ sets the equilibrium adhesion patch size, as shown in FIG. 2A. For clarity, the model is simplified to neglect emulsion polydispersity and volume conservation upon deformation. The work done by the external pressure on the droplets is given by W1=Fd, wherein F is the interdroplet force, and the distance between the droplet centers and R0, or the undeformed radius, is given by Equation (II):

$$d = R_0\left(\frac{h}{R_0} + 2 - \theta + \frac{5}{24}\theta^4\right) \qquad (II)$$

This compression model does work against the energy of deformation given in Equation (III)

$$E_d = \frac{1}{2\sigma\pi R_0^2 \theta^4} \qquad (III)$$

wherein σ is the surface tension. Moreover, the work done in bringing the surfaces closer together serves to overcome electrostatic repulsion, modeled as in Equation (IV), wherein ∈ is the dielectric constant, $\psi_0$ is the electrical potential at the droplet surface, and K is the inverse of the Debye length.

$$Ee = 2\pi \in \psi_0^2 R_0 \exp(-\kappa h) \qquad (IV)$$

If the resulting interparticle distance h is smaller than a critical length $h_c$, the interaction of the surface proteins leads to an adhesive state with an additional binding energy term. The distance $h_c$ of about 18 nm is set by the size of the biotinylated lipids and the streptavidin between them. The binding energy is given by Equation (V), wherein $e_b = C_b \in_b$ is the binding energy per unit area, $C_b$ is the binder concentration in the adhesion patch, $\epsilon_b$ is the binding energy of an individual binder, and H(t) is the Heaviside function that determines whether binding is allowed.

$$E_b = e_b R_0^2 \left(\theta^2 - \frac{1}{3}\theta^4\right) H(h_c - h) \quad \text{(V)}$$

The resulting energy landscape reveals two local minima, $E_1=E(\theta_1; h_1)$ and $E_2=E(\theta_2; h_2)$, corresponding to the deformed yet non-adhesive and adhesive states of the contacting droplets. These energy states are separated by an energy barrier and a discontinuity at h=hc that comes from the additional binding energy Eb for $h<h_c$, as shown in FIG. 2B. Adhesion can only occur if the global minimum is found at $h<h_c$ or if the energy difference between the two minima is within thermal energy. Decreasing the Debye length or compressing droplets with force F modifies the energy landscape in favor of the adhesive state, as shown in FIG. 2C. The parameters are varied throughout the experiment as detailed in Example 2 and FIG. 5.

Figure 1B:
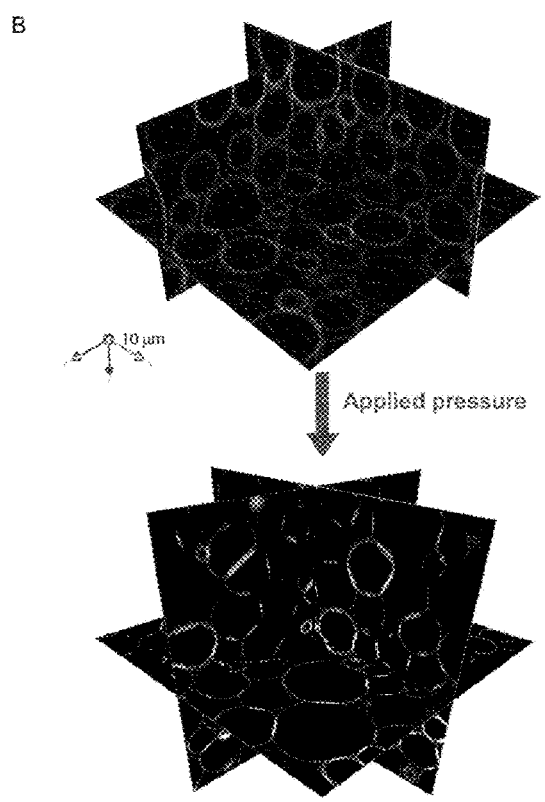
FIG. 1(B) is a three-dimensional representation of confocal images showing Texas Red-stained streptavidin fluorescence on the surface of the droplets. Packing under gravity, which does not create adhesion, is shown, whereas applied pressure triggers formation of adhesions between droplets, shown as areas of brighter fluorescence.

To prepare the emulsion for use in the model, the oil droplets were prepared with egg L-α-phosphatidylcholine (EPC) lipids and the DSPEPEG(2000) biotinylated lipids (Avanti Polar Lipids, Alabaster, Ala.) at a molar ratio of 92:8, respectively, and a total mass of 19 mg. The solvent containing the lipids was evaporated under nitrogen before 10 mL of silicone oil was added to the dried lipids. This mixture was then sonicated during 30 minutes at room temperature and heated at 50° C. over 3 hours. After cooling to room temperature the lipid containing oil (10 mL) was first coarsely emulsified in 22 mL of buffer (5 mM SDS, wt 18% of 100 um, and sheared at 22 rpm. The resulting emulsion was washed twice in an aqueous solution of 1 or 5 mM SDS before a last wash in the index matching buffer containing 50:50 glycerol:water. This emulsion is stable over several weeks at 4° C. The emulsion was dyed on the surface with Texas Red conjugated streptavidin (Invitrogen), 500 uL of 1 or 5 mM SDS emulsion was mixed with 1 mg/mL streptavidin (25 μL) and 1.5 mL of buffers containing 2 mM Tris pH=7, 1 or 5 mM SDS, 0 to 30 mM NaCl. This solution was incubated one hour at room temperature to allow the streptavidin to bind to the biotinylated lipids on the droplets. The sample was observed after creaming under gravity as shown in FIG. 1B or centrifuged at 20° C. at accelerations ranging from 50 to 1400 g over 20 minutes. The top layer of the compressed emulsion was then transferred into another observation cell to isolate it from the continuous phase and therefore avoid relaxation. The samples were imaged using a fast scanning confocal microscope (Leica TCS SP5 II).

Example 2: Quantitative Analysis of Force-Dependent Adhesion

In order to compare the experimental findings with the modeled data, approximately 1000 adhesion patches were extracted from three-dimensional reconstructions of confocal images. As shown in FIG. 3A, the adhesion patches were identified by a thresholding algorithm because they fluoresce brighter than the surface of the droplets or the aqueous background. The homogeneous spatial distribution of the adhesion discs within the volume of the packing is shown in FIG. 3B in a typical experiment. For every droplet pair in contact, the adhesion patch radius $r_p$ was measured. The images revealed the radius of deformation rd between contacting droplets from the geometric overlap between the identified spheres of radius R shown in FIG. 3C. Whereas the adhesion patch spans the full area of deformation in the theoretical model, experimentally observed results indicated that $r_p<r_d$. Rather, $r_p=\alpha r_d$ with the slope α giving the coverage of the adhesion as shown in FIG. 3D. The $r_p$, $r_d$, and R values measured, together with the parameters delineated in Example 1 were used to obtain the value of work done in compressing each droplet pair, wherein the work is given by Equation VI, and the corresponding interdroplet force $F_1$.

$$W_1 = E_e = E_d - E_b \quad \text{(VI)}$$

wherein $W_1$ is the work done in compressing each droplet pair, $E_b$ is binding energy, $E_e$ is electrostatic repulsion, and $E_d$ is the energy of deformation.

Electrostatic repulsion, surface tension, and how the screening of charges influences the force-dependent adhesion in terms of the timescale, size, and number density of the protein links, were all tested. By varying the SDS concentration from 1 to 5 mM in the emulsions, we simultaneously increase the charge repulsion and decrease the surface tension of the droplets. In the 5 mM case, the charge repulsion prevents adhesion under gravity (FIG. 4Ai) and requires an applied pressure by centrifugation as well as a long waiting time for patch formation (FIG. 4Aii). The fact that patches persist after relaxing the applied pressure to 0.2 kPa, corresponding to gravitational compression, confirms that they arise from protein links across contacting surfaces (FIG. 4Aiii). This irreversibility indicates a kinetic barrier to removing the adhesive patches. The mean patch radius grows towards steady state size to form adhesions on a characteristic timescale of hours, as shown in FIG. 4B, where the patch growth dynamics is displayed for two different global pressures. The timescales on the order of hours are significantly slower than minutes encountered in individual cellular adhesions, or seconds in functionalized model membranes. However, centrifugation-based bulk measurements of the kinetics of cell-cell adhesion reach a plateau after 90 minutes, similar to the approximately 120 minutes measured under low emulsion compression. Decreasing the electrostatic repulsion patches by lowering the SDS concentration to 1 mM or by screening charges with salt leads to patches growing on much faster timescales (below 20 minutes), independent of the centrifugation rate (FIG. 4Cii-vi).

Image analysis of the local microstructure was then conducted, which revealed the dependence of each patch size on the corresponding interdroplet force. To probe a wide range of forces, each emulsion was centrifuged at different rates, and multiple stacks were imaged to collect a large statistical pool of data. Higher compression visibly increases the adhesion patch sizes under all conditions, as shown in FIG. 4C iii and iv. To quantify the effect, the local interdroplet forces were measured, and the corresponding average patch size as a function of the average force for all conditions was plotted as shown in FIG. 4D. In all cases, the increase of patch size with load force follows the model prediction of a square root law at high forces, but there is a pronounced deviation towards larger patches at low forces due to the onset of protein binding. This result demonstrates that mechanical compression is sufficient to induce cell-cell adhesion strengthening, in addition to the active forces exerted by actin polymerization. While the force-dependence is similar between the data sets, they differ in the prefactor. This prefactor corresponds to the adhesion coverage α of the area of deformation identified in FIG. 3D, which is larger for the 5 mM SDS emulsion with salt. This demonstrates that the line tension develops as the protein complexes displace the other surface molecules and increase the local surface tension, similar to the emulsion and the resulting line tension. In cell-cell adhesion, such a line tension could account for the initial cadherin accumulation into small puncta that spread across the interface over time.

Although the increase of patch sizes with force follows the model prediction independent of the emulsion conditions, the fraction of droplets contacts that are covered with adhesion patches Np=Nc reveals interesting distinctions, as shown in FIG. 5A. In the absence of screening by salt, no patches are observed in the 1 mM and 5 mM SDS emulsion under gravitational compression with forces of approximately 15 pN (corresponding to deformations below the resolution limit of the microscope). Applying the smallest measurable force of approximately 2 nN leads to 20% and 35% of droplet contacts with adhesions, respectively. This result is consistent with the force tilting the energy landscape in the model to favor the adhesive minimum. However, the low probability of adhesion remains constant over the entire force range up to 50 nN, which indicates a kinetic barrier that is insensitive to force. Instead, this barrier can be overcome by screening the electrostatic repulsion with 10 mM salt, which allows some adhesions (5%) to form even under gravity. Upon compression of the screened emulsions, the probability of adhesion reaches almost 1, also evidenced by the large model are shown in FIG. 2C for the 5 mM SDS emulsion. They highlight the importance of homeostatic pressure in achieving the mechanical integrity of tissues. An alternative to using force to populate droplet contacts with adhesions is to screen the charges by increasing the salt concentration, as shown in FIGS. 5B and 4Civ. This trend is in agreement with the model, in which the corresponding decrease in the Debye length changes the energy landscape, favoring the adhesive state and decreases the barrier to it. Since the model assumes a constant compression force of 15 pN between droplets, the transition appears sharper than in the emulsion where the patch fraction is derived from a distribution of forces in a given droplet packing under gravity. Under physiological conditions of 100 mM salt, the model predicts the spontaneous nucleation of adhesions in both emulsions. Under gravity alone, the model predicts adhesions on the scale of 200 nm in radius from the estimated concentration of cadherins on the cell surface. While such small adhesions are sufficient to trigger a biochemical response in the cell, they cannot maintain the mechanical integrity of tissues. As shown above, nanoNewton forces are necessary to grow adhesions that span the entire cell-cell interface.

Example 3: Phase Diagram for Adhesion

Finally, a phase diagram was constructed for adhesion from the probabilities of forming a patch as a function of the applied force and the concentration of NaCl, as shown in FIG. 5C for the 5 mM SDS emulsion. The model prediction of the phase diagram, fixed by literature values for the surface tension of our emulsions, the binding energy per literature values for the surface tension of the present emulsions, the binding energy per streptavidin-biotin bond and the measured value for the electrical potential, yields a binder concentration of 47 molecules/um2 in the 5 mM SDS case and 60 molecules/um2 in the 1 mM SDS case to fit the phase boundaries identified by the data. This range of binder densities is similar to that of cadherins (80-800 molecules/um2) on the cell surface. Indeed, all the parameters that describe the biomimetic system are to within a factor of two in agreement with the values measured in cells under physiological conditions, indicating that the present system provides a good model for biological study. The predicted boundary between the adhesive and non-adhesive regions in phase space explains why cell aggregates either spread like a viscoelastic medium or disperse like an assembly of particles depending on the adhesion properties of the cell-cell interactions. While it is known that the concentration of adhesive molecules on the cell surface tune the strength of adhesion, the present system shows how the concentration, membrane surface tension and cytoskeletal pushing forces as well. More specifically, the phase diagram demonstrates that the global screening of charges present in the cellular environment facilitates the formation of adhesions, but external highlights the possible role of adhesion in tumor progression, since homeostatic pressure affects its growth and metastasis.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A biomimetic system comprising:
   at least two functionalized emulsion droplets, each having an interfacial phospholipid component with an inward facing hydrophobic tail and an outward facing hydrophilic head, a polymer to induce steric repulsion, and a ligand bound to the hydrophilic head that facilitates adhesion;
   a surfactant causing electrostatic repulsion,
   an aqueous phase of the emulsion comprises an agent with a functional group that binds to the ligand, and
   the at least two functionalized emulsion droplets interconnected by the agent bound to the ligand;
   wherein the phospholipid component facilitates the formation of at least two emulsion droplets.

2. The system of claim 1, wherein the ligand is selected from the group of a cadherin and a biotin.

3. The system of claim 1, wherein the agent comprises a streptavidin.

4. The system of claim 1, wherein the interfacial phospholipid component comprises an egg phosphatidylcholine.

5. The system of claim 1, wherein the surfactant comprises a sodium dodecyl sulfate ionic surfactant.

6. The system of claim 1, wherein the polymer is selected from the group consisting of polyethylene glycol (PEG), polypropylene glycol (PPG), carbohydrate polymer, amino acid polymer or polyvinyl pyrolidone.

7. The system of claim 1, wherein the polymer and the ligand form a single surface active complex.

8. The system of claim 1, wherein the agent, once bound to the ligand of one droplet surface, diffuses until it binds to another agent on a neighboring droplet.

9. The system of claim 8, wherein force is applied to the system in an amount sufficient to reduce the interparticle distance h to be smaller than a critical length hc, wherein below which distance interaction of the surface active agents produces an adhesive state in each of the at least two functionalized emulsion droplets.

10. The system of claim 9, wherein the ligand is selected from the group of a cadherin and a biotin, the agent is streptavidin, and hc is about 18 nm.

11. The system of claim 9, wherein the force is applied either via centrifuge or the addition of a salt.

12. The system of claim 1, further comprising a fluorescent dye to add color to the emulsion.

13. The system of claim 1, wherein the two functionalized emulsion droplets have a diameter between 4 and 20 microns.

* * * * *